United States Patent
Monaghan et al.

(10) Patent No.: US 9,746,405 B2
(45) Date of Patent: Aug. 29, 2017

(54) METHOD FOR ELEMENTALLY DETECTING VARIATIONS IN DENSITY

(71) Applicant: GENERAL ELECTRIC COMPANY, Schenectady, NY (US)

(72) Inventors: Philip Harold Monaghan, Hockessin, DE (US); Clifford Bueno, Clifton Park, NY (US); Jonathan Immanuel Sperl, Freising (DE); Cristina Francesca Cozzini, Munich (DE)

(73) Assignee: General Electric Company, Schenectady, NY (US)

( * ) Notice: Subject to any disclaimer, the term of this patent is extended or adjusted under 35 U.S.C. 154(b) by 403 days.

(21) Appl. No.: 14/274,160

(22) Filed: May 9, 2014

(65) Prior Publication Data

US 2015/0323439 A1 Nov. 12, 2015

(51) Int. Cl.
*G01N 23/00* (2006.01)
*G01N 9/24* (2006.01)
(Continued)

(52) U.S. Cl.
CPC .............. *G01N 9/24* (2013.01); *G01N 23/04* (2013.01); *G01N 23/046* (2013.01);
(Continued)

(58) Field of Classification Search
CPC . A61B 6/484; G01N 23/046; G01N 23/20075
See application file for complete search history.

(56) References Cited

U.S. PATENT DOCUMENTS 7,486,770 B2  2/2009  Baumann et al.
7,889,838 B2  2/2011  David et al.
(Continued)

FOREIGN PATENT DOCUMENTS

WO  2012000694 A1  1/2012

OTHER PUBLICATIONS

M. Robinson, Characterizing the Nova600 microfocus X-ray source for use with the Talbot interferometer for phase-contrast imaging, Department of Physics, Lewis & Clark College, Portland, OR, dated Aug. 19, 2010.
M. Burnett, The Automatic Analysis of Interferometric Data—FRAN, Description and User Guide, The Univeristy of Warwick, School of Engineering, Optical Engineering Laboratory 1996.
M. Bech, Experimental validation of image contrast correlation between ultra-small-angle X-ray scattering and grating-based dark field imaging using a laser-driven compact X-ray source, Photon Lasers Med 1 (2012): 47-50, Copyright 2012 by Walter de Gruyter, Berlin, Boston. DOI 10.1515/plm-2011-0012.
(Continued)

*Primary Examiner* — Dani Fox
(74) *Attorney, Agent, or Firm* — McNees Wallace & Nurick LLC (57) ABSTRACT

A method and system are provided for elementally detecting variations in density. The method includes providing a computed tomography device, comprising a radiation source, a detector, and at least one grating between the radiation source and the detector, positioning the component between the radiation source and the detector, directing radiation from the radiation source to the detector to acquire information from the component, generating at least one phase contrast image and at least one dark field contrast image of the component corresponding to variations in density with the information from the component, correlating the variations in density to a foreign mass, and displaying foreign mass distribution within the component. The system includes a radiation source, a detector, a component, a first grating, a second grating, and an analysis device capable of determining total variation of density in response to radiation received by the detector, and correlating the variation of density to free element distribution in the component.

15 Claims, 4 Drawing Sheets

(51) Int. Cl.
*G01N 23/04* (2006.01)
*G01T 1/29* (2006.01)
(52) U.S. Cl.
CPC ...... *G01T 1/2985* (2013.01); *G01N 2223/419* (2013.01); *G01N 2223/652* (2013.01)

(56) References Cited

U.S. PATENT DOCUMENTS

| | | | | |
|---|---|---|---|---|
| 2012/0076927 | A1* | 3/2012 | Bhatt | C04B 35/565 427/122 |
| 2013/0094625 | A1* | 4/2013 | Huang | A61B 6/484 378/6 |
| 2015/0153290 | A1* | 6/2015 | Mukaide | G01N 23/083 378/62 |

OTHER PUBLICATIONS

F. Pfeiffer, Hard X-Ray Phase Tomography with Low-Brilliance Sources, Physical Review Letters 98, 108105 (2007) DOI:10.1103/PhysRevLett.98.108105.
P. Zhu, Low-dose, simple, and fast grating-based X-ray phase-contrast imaging, www.pnas.org/cgi/doi/10.1073/pnas.1003198107.
T. Weitkamp, X-ray phase imaging with a grating interferometer, Optics Express 6296, Aug. 8, 2005, vol. 13. No. 16.

* cited by examiner

METHOD FOR ELEMENTALLY DETECTING VARIATIONS IN DENSITY

FIELD OF THE INVENTION

The present invention is directed to a method for elementally detecting variations in density. More specifically, the present invention is directed to a method for detecting foreign masses of a disparate density in ceramic matrix composite materials.

BACKGROUND OF THE INVENTION

Due to their high temperature capabilities, ceramic matrix composite (CMC) materials are often desirable in components operating under elevated temperatures. CMC materials generally comprise a ceramic fiber reinforcement material embedded in a ceramic matrix material. The reinforcement material may be discontinuous short fibers dispersed in the matrix material, continuous fibers, or fiber bundles oriented within the matrix material, and serves as the load-bearing constituent of the CMC. In turn, the ceramic matrix protects the reinforcement material, maintains the orientation of its fibers, and serves to dissipate loads to the reinforcement material.

Often, the fabrication of CMCs includes using multiple prepreg layers formed by impregnating a desired ceramic fiber reinforcement material with a slurry containing one or more precursors of the CMC matrix material, and organic resin binders. The one or more precursors are selected based upon a desired composition for the ceramic matrix of the CMC component. For example, the precursors for silicon-based composites, such as silicon carbide (SiC), which are of particular interest for high-temperature applications, include SiC powder and/or one or more carbon-containing materials that are ultimately converted to SiC upon reaction with molten Si. However, during the production of the SiC CMC components, some of the molten silicon may not react with other contents of the matrix, resulting in free elemental silicon and/or silicon alloy.

Current methods for determining the amount of free silicon often require destruction of the sample or component being tested. For example, one method includes dissolving the samples in an acid that does not affect silicon. Not only is dissolving the sample costly from both a time and raw material perspective, it also presents some element of danger. Other methods, such as Atom Probe Tomography and Secondary Ion Mass Spectroscopy, also require the sample component be destroyed.

A method and an article with improvements in the process and/or the properties of the components formed would be desirable in the art.

BRIEF DESCRIPTION OF THE INVENTION

In one exemplary embodiment, a method for elementally detecting variations in density within a component includes providing a computed tomography device, comprising a radiation source, a detector, and at least one grating between the radiation source and the detector, positioning the component between the radiation source and the detector, directing radiation from the radiation source to the detector to acquire information from the component, generating at least one phase contrast image and at least one dark field contrast image of the component corresponding to variations in density with the information from the component, correlating the variations in density to a foreign mass, and displaying foreign mass distribution within the component.

In another exemplary embodiment, a method for detecting free elements in a ceramic matrix composite component includes providing a computed tomography device, comprising a radiation source, a detector, a first grating positioned between the radiation source and the detector, and a second grating positioned between the first grating and the detector, positioning the ceramic matrix composite component between the radiation source and the first grating, rotating the ceramic matrix composite component to provide a plurality of component positions, stepping the first grating or the second grating at each component position in the plurality of component positions to provide phase steps, directing radiation from the radiation source to the detector at each phase step of each component position in the plurality of component positions to acquire information from the ceramic matrix composite component, generating phase contrast and dark field contrast images corresponding to variations in density with the information from the ceramic matrix composite component, correlating the variations in density to at least one free element, and displaying distribution of the at least one free element within the ceramic matrix composite component.

In another exemplary embodiment, a system for elementally detecting variations in density within a component includes a radiation source, a detector, the component positioned between the radiation source and the detector, a first grating positioned between the component and the detector, a second grating positioned between the first grating and the detector, and an analysis device capable of determining the variations in density in response to radiation received by the detector, and correlating the variations in density to free element distribution in the component. The radiation is emitted from the radiation source and travels through the component, the first grating, and the second grating prior to being received by the detector.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are a method and a system for detecting foreign masses of a disparate density within a component. Embodiments of the present disclosure, in comparison to methods and systems not using one or more of the features disclosed herein, form both phase contrast and dark field contrast images of a ceramic matrix composite component, determine an amount of a foreign mass in a component without destroying the component, determine a distribution of a foreign mass in a component without destroying the component, or a combination thereof.

Figure 1:
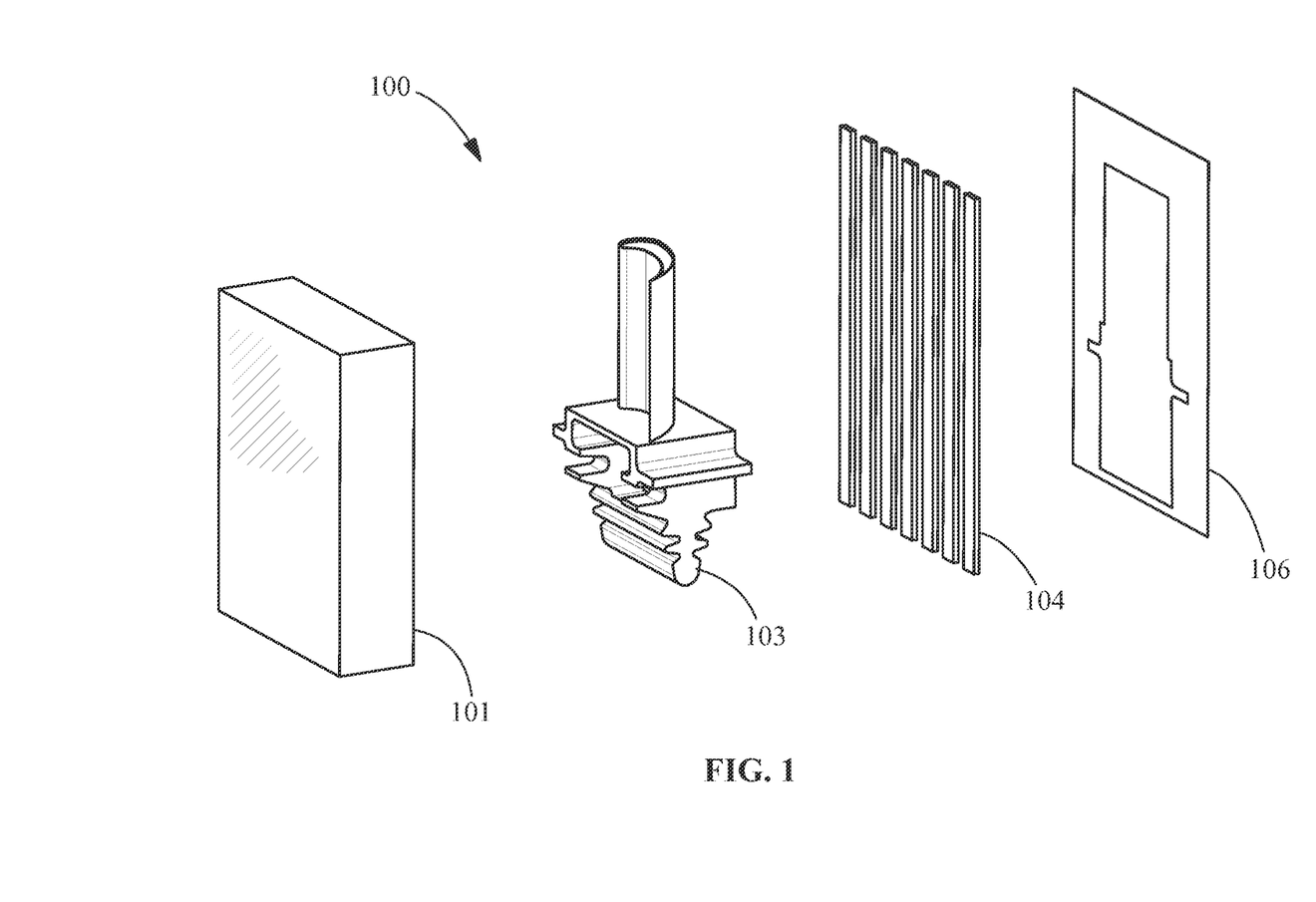
FIG. 1 is a schematic view of a system having a single grating for elementally detecting density within a component according to an embodiment of the disclosure.
Figure 2:
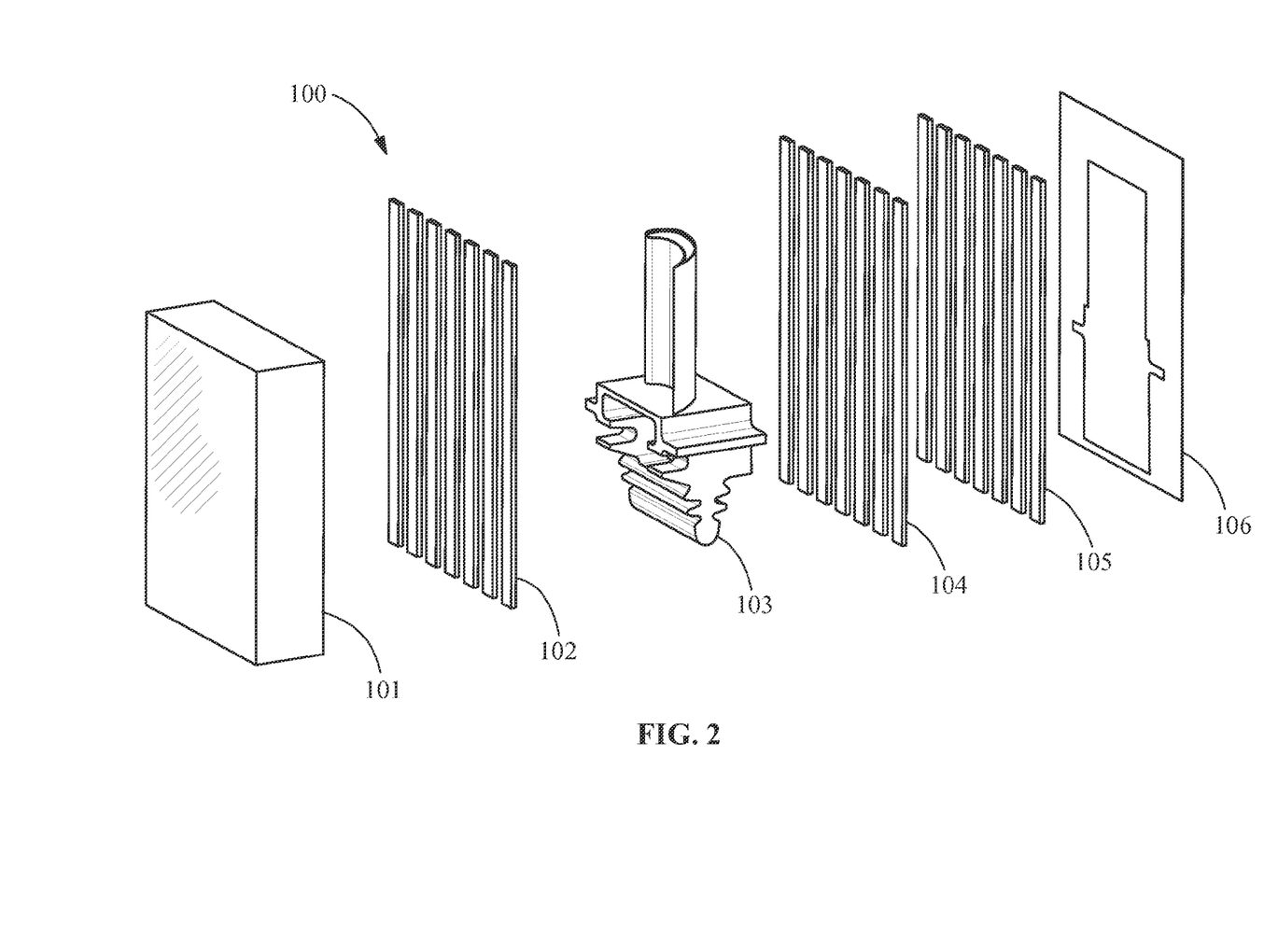
FIG. 2 is a schematic view of a system having multiple gratings for elementally detecting density within a component according to an embodiment of the disclosure.

Referring to FIGS. 1 and 2, a system 100 for elementally detecting density includes a computed tomography device and a component 103, the computed tomography device having at least a radiation source 101, a first grating 104, and a detector 106. The component 103 and the first grating 104 are positioned between the radiation source 101 and the detector 106. The first grating 104 is either positioned between the component 103 and the detector 106, as shown in FIG. 1, or between the radiation source 101 and the component 103 (not shown). The first grating 104 includes a phase grating that divides radiation from the radiation source 101 into diffracted beams. The radiation source 101 includes, but is not limited to, a coherent radiation source or an incoherent radiation source. In one embodiment, as shown in FIG. 2, a source grating 102 is positioned between the radiation source 101 and the component 103. The source grating 102 provides coherence to the system 100, such as, for example, when the radiation source 101 includes the incoherent radiation source.

Without wishing to be bound by theory, downstream of the first grating 104, the diffracted beams interfere to form linear periodic fringe patterns that are recorded by the detector 106. In one embodiment, the fringe patterns are resolved by the detector 106, such as, for example, when the detector 106 includes a pixel size of 1 micron or less. In an alternate embodiment, as shown in FIG. 2, a second grating 105 is positioned between the first grating 104 and the detector 106 to resolve the fringe patterns. The second grating 105 includes an absorption grating that provides a transmission mask for the detector 106, transforming the fringes into variations in signal intensity.

The first grating 104 includes any suitable material for diffraction, such as, but not limited to, nickel, silicon, or a combination thereof. The second grating 105 includes any suitable material for absorption, such as, but not limited to, gold. In one embodiment, the first grating 104 and the second grating 105 are arranged to position lines of the first grating 104 parallel with lines of the second grating 105. In another embodiment, the first grating 104 includes a larger pitch as compared to the second grating 105. For example, in a further embodiment, the first grating 104 is a silicon grating having a pitch of 4 µm, and the second grating 105 is a silicon grating with grooves electroplated by gold, the second grating 105 having a pitch that is equal to half the pitch of the first grating 104.

The source grating 102, the first grating 104, and/or the second grating 105 are planar, 2-dimensional, curved, or a combination thereof. In one embodiment, a curved grating is curved in one or two planes, and includes a center of curvature positioned on an optical axis at a focal point of the radiation source 101. In another embodiment, the curved gratings are curved through clamping or use of a flexible grating. The curved grating includes radially aligned bars that reduce or eliminate a shadowing effect of flat gratings at high cone angles. In an alternate embodiment, the source grating 102, the first grating 104, and/or the second grating 105 includes a flat grating with radially aligned structuring. The center of the flat grating is positioned on the optical axis of the radiation source 101, and produces both one-dimensional and two-dimensional grating structures via grating bars and gaps oriented in an inclined fashion.

The component 103 includes, but is not limited to, a ceramic matrix composite (CMC), a metal matrix composite (MMC), a component including silicon (Si), any other component including a foreign mass, or a combination thereof. For example, in one embodiment, the component 103 includes a silicon carbide (SiC) CMC. It was unexpectedly discovered that using the system 100 described above, variations in density within the component 103 are detected elementally. Based upon the variations in density, the system 100 detects foreign masses of a disparate density within the component 103. The foreign masses include, but are not limited to, micro inclusions, free elements (e.g., free silicon), or any other element that is not related to a ceramic matrix composite. In one embodiment, by correlating the elementally detected variations in density to a free element, the system 100 provides a free element distribution within the component 103. For example, in one embodiment, the system 100 generates an image that displays a distribution of elemental silicon using differences in density as shown by a contrast to noise ratio, where a change in contrast between the elemental Si and the substrate of the component 103 is compared with respect to the noise.

Figure 3:
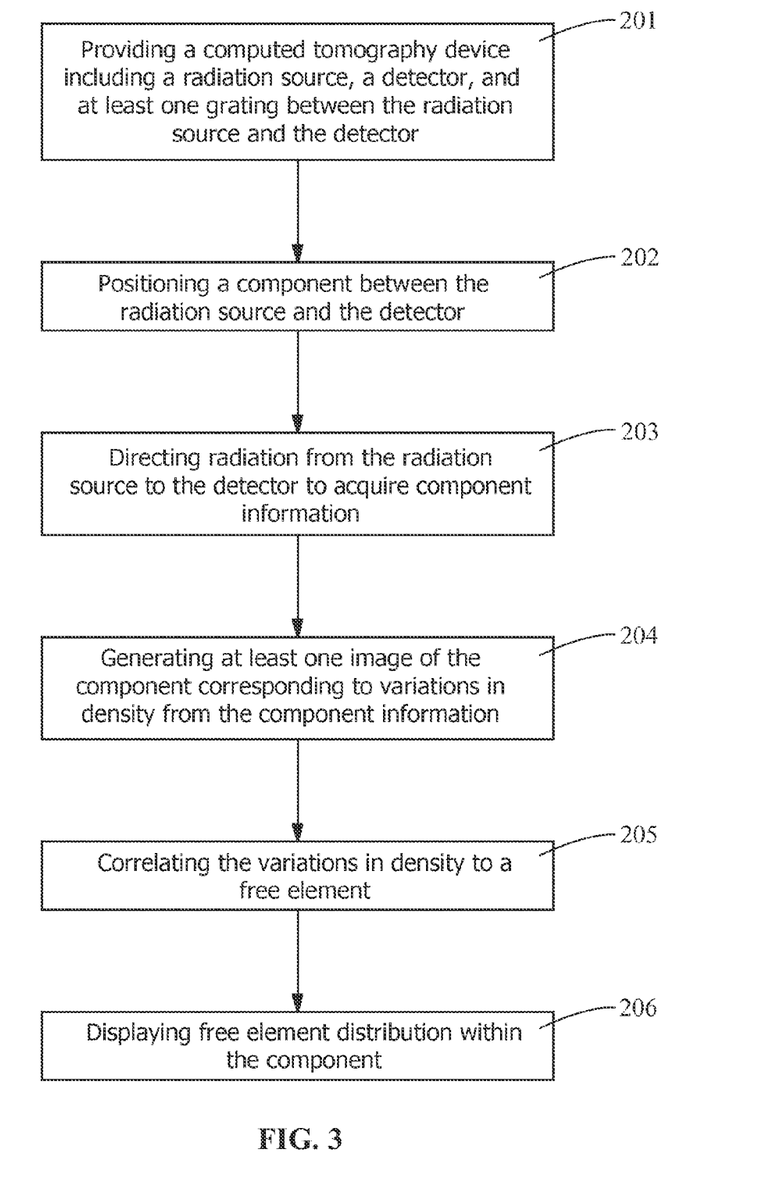
FIG. 3 is a flow chart for a method of determining an amount of an element within a component according to an embodiment of the disclosure.

Referring to FIGS. 1-3, based upon the ability to elementally view variations in density, a method 200 for determining an amount and/or distribution of an element within the component 103 has been developed. In one embodiment, the method 200 includes providing a computed tomography device (step 201) including the radiation source 101, the detector 106, and at least one grating between the radiation source 101 and the detector 106; positioning the component 103 (step 202) between the radiation source 101 and the detector 106; directing radiation (step 203) from the radiation source 101 to the detector 106 to acquire component information; generating the at least one image (step 204) of the component 103 corresponding to variations in density and refractive index from the component information; correlating the variations in density (step 205) to a free element; and displaying free element distribution (step 206) within the component 103.

The radiation from the radiation source 101 forms an incident wave or beam, which travels through the component 103, the first grating 104, and/or the second grating 105 before reaching the detector 106. Information regarding the incident wave or beam, such as, but not limited to, a phase, an amplitude of oscillation, and/or an average intensity, is recorded by the detector 106. When the component 103 is positioned between the radiation source 101 and the detector 106, the component 103 causes changes in the incident wave or beam travelling traveling there through. At least one image of the component 103 is then generated based upon a comparison of the information recorded when the component 103 is present with information recorded when the component 103 is not present. For example, the at least one image of the component 103 is generated based upon changes such as, but not limited to, a phase shift, a change in the amplitude of oscillation, and/or a change in the average intensity, as recorded by the detector 106.

In one embodiment, the method 200 includes a phase stepping method using the first grating 104 or the second grating 105. During the phase stepping method, either the first grating 104 or the second grating 105 is stepped, or moved incrementally, along a transverse direction of the system 100. The stepping of the first grating 104 or the second grating 105 separates the phase shift information of the component 103 from other contributions, such as, but not limited to, absorption by the component 103, imperfections of the first grating 104 and/or the second grating 105, non-uniform illumination, or a combination thereof. The fringe patterns, as transformed by the second grating 105, are mapped to the detector 106 and recorded as part of the information regarding the incident wave or beam. In one embodiment, the fringe patterns include, but are not limited to, sinusoidal fringes. The sinusoidal fringes contain quantitative information about a phase gradient of the component 103, which is used to generate the image of the component 103.

Any suitable combination of system parameters, radiation source parameters, and detector parameters is used to perform a scan with the system 100 and generate the image of the component 103. For example, in one embodiment, the system parameters include a design energy voltage, a grating distance, and a Talbot order. Suitable design energy voltages include, but are not limited to, between 10 kV and 50 kV, between 10 kV and 40 kV, between 20 kV and 30 kV, 25 kV, or any combination, sub-combination, range, or sub-range thereof. Suitable grating distances include, but are not limited to, up to about 4 meters, between 0.5 and 3 meters, between 1 meter and 3 meters, up to about 2 meters, 1 meter, or any combination, sub-combination, range, or sub-range thereof.

The radiation source parameters include, for example, a voltage, a current, and a target. In one embodiment, as the voltage of the radiations source parameters is increased, the visibility of the first grating 104 and/or the second grating 105 may be decreased, providing an upper limit on the voltage of the radiation source 101. For example, in another embodiment, suitable voltages include, but are not limited to, between 10 kVp and 100 kVp, between 10 kVp and 75 kVp, between 25 kVp and 75 kVp, between 10 kVp and 50 kVp, between 25 kVp and 50 kVp, 50 kVp, or any combination, sub-combination, range, or sub-range thereof. Suitable currents include, but are not limited to, between 5 mA and 30 mA, between 5 mA and 20 mA, between 5 mA and 15 mA, 10 mA, or any combination, sub-combination, range, or sub-range thereof. Suitable targets include, but are not limited to, W, Ag, Au, or a combination thereof The detector 106 includes any suitable detector for detecting radiation from the radiation source 101, such as, but not limited to, a cadmium telluride (CdTE) detector, a cadmium zinc telluride (CZT) detector, a silicon (Si) detector, a germanium (Ge) detector, a gallium arsenide (GaAs) detector, a lead oxide (PbO) detector, or any other detector including a suitable pixel size. The detector parameters include a pixel size of, for example, 25 µm, 50 µm, 100 µm, 200 µm, 400 µm, or any other suitable pixel size.

Acquisition parameters for acquisition of the information with the system 100, performed with any suitable combination of the system parameters, the radiation source parameters, and the detector parameters, include magnification, exposure duration, phase steps, and number of component positions. The magnification of the system 100 is selected based upon the pixel size of the detector 106 and/or the specifics of the component 103. For example, in one embodiment, the system 100 includes a magnification of 10 to provide $1/10^{th}$ the pixel size of the detector 106. Other magnifications include, but are not limited to, up to 50 times, up to 100 times, or at least 100 times.

Each of the component positions corresponds to a different perspective provided by an initial component position, incremental rotation of the component 103 with respect to the computed tomography device, and/or incremental rotation of the computed tomography device with respect to the component 103. In one embodiment, the incremental rotation of the component 103 and/or the computed tomography device provides up to a 360 degree view of the component 103. At each of the component positions the phase steps and the exposure duration collect the information corresponding to the different perspective. Any suitable number of phase steps is performed at each of the component positions. A suitable number of phase steps includes, for example, 5 phase steps, 10 phase steps, 20 phase steps, or any other number of phase steps for providing a desired image. Suitable exposure durations include, but are not limited to, between 1 and 20 seconds, between 1 and 10 seconds, between 5 and 10 seconds, or any combination, sub-combination, range, or sub-range thereof Based upon the incremental rotation and the number of phase steps, a single scan provides up to at least 4,000 views of the component 103.

For example, in one embodiment, the acquisition of the information includes 360 views, 40 phase steps per view, and 10 seconds of exposure for each of the phase steps. In another embodiment, the acquisition is performed with the system parameters including the design energy voltage of 25 kV, the grating distance of 1 meter, and the $1^{st}$ Talbot order. In a further embodiment, the acquisition is performed with the radiation source parameters including the voltage of 50 kVp, the current of 10 mA, the Ag target, and the CdTE detector having the pixel size of 100 µm.

Figure 4:
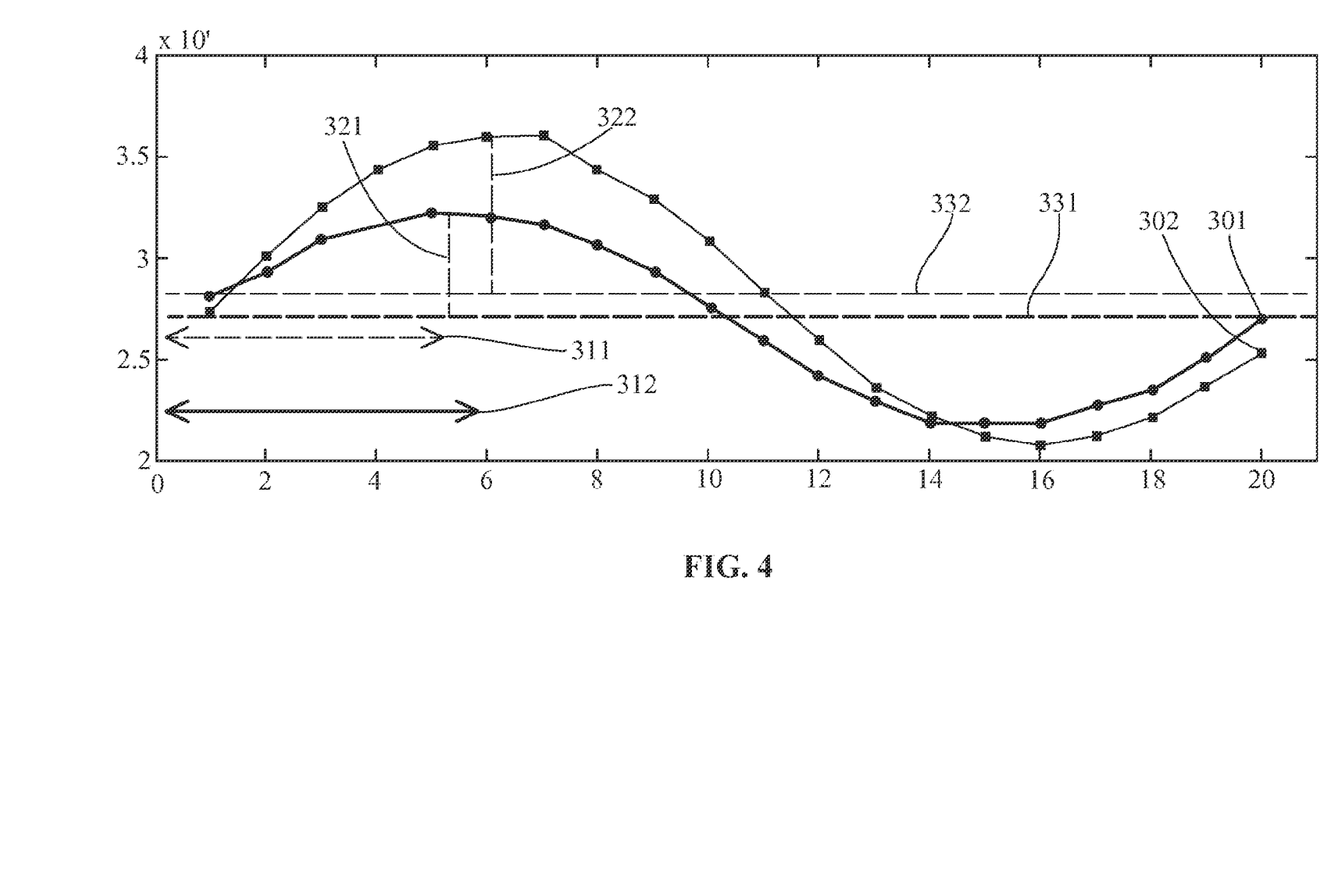
FIG. 4 is an exemplary graph of the information collected by the system of FIG. 2.

Referring to FIG. 4, in one embodiment, an absorption image, a phase contrast image, and a dark field contrast image are generated from the sinusoidal fringes recorded by the detector 106. Without wishing to be bound by theory, dark field contrast imaging is an inherently scattering based method used to determine optical characteristics that are generally unobservable in bright-field. The absorption image, the phase contrast image, and the dark field contrast image are generated based upon a comparison of a component measurement 301 (i.e., the information recorded from the system 100 including the component 103) to an air measurement 302 (i.e., the information recorded from the system 100 without the component 103). The component measurement 301 provides a component oscillation phase 311 ("$\phi_{cmp}$"), a component amplitude of oscillation 321 ("$\alpha_{1,cmp}$"), and a component average intensity 331 ("$\alpha_{0,cmp}$"). The air measurement 302 provides an air oscillation phase 312 ("$\phi_{air}$"), an air amplitude of oscillation 322 ("$\alpha_{1,air}$"), and an air average intensity 332 ("$\alpha_{0,air}$"). The three component quantities (i.e., the component oscillation phase 311, the component amplitude of oscillation 321, and the component average intensity 331) are obtained by a Fourier analysis of the component measurement 301, such as, for example, by determining the zeroth and first harmonic of a curve measured in the component measurement 301. The three air quantities (i.e., the air oscillation phase 312, the air amplitude of oscillation 322, and the air average intensity 332) are obtained by a Fourier analysis of the air measurement 302, such as, for example, by determining the zeroth and first harmonic of a curve measured in the air measurement 302.

To generate the absorption image, the component average intensity 331 is divided by the air average intensity 332, as shown in Equation 1 below. To generate the phase contrast image, the air oscillation phase 312 is subtracted from the component oscillation phase 311, as shown in Equation 2 below. To generate the dark field contrast image, the ratio of the component amplitude of oscillation 321 and the component average intensity 331 is divided by the ratio of the air amplitude of oscillation 322 and the air average intensity 332, as shown in Equation 3 below.

$$\alpha_{0,cmp}/\alpha_{0,air} \quad \text{Equation 1}$$

$$\phi_{cmp} - \phi_{air} \quad \text{Equation 2}$$

$$(\alpha_{1,cmp}/\alpha_{0,cmp})/(\alpha_{1,air}/\alpha_{0,air}) \quad \text{Equation 3}$$

The dark field contrast image generated from the component measurement 301 and the air measurement 302, using Equation 3, provides different contrast as compared to the phase contrast image generated using Equation 2.

In one embodiment, the phase contrast image and the dark field contrast image display elemental variations in density within the component 103. In another embodiment, the elemental variations in density are correlated with free elements, such as, but not limited to, elemental silicon, or "free silicon". In a further embodiment, based upon the correlation of the free elements with the elemental variations in density, the phase contrast image and the dark field contrast image display a nature, the amount, and/or the distribution of the free elements within the component 103. For example, in one embodiment, as lower densities appear darker in the dark field contrast image, the free Si, having a density of 2.33 g/cm$^3$, appears darker as compared to the SiC, having a density of 3.21 g/cm$^3$. Based upon variations in brightness, the free Si is correlated with portions of the phase contrast image and the dark field contrast image to display the nature, the amount, and/or the distribution of the free Si within the component 103.

When the component 103 includes plies separated by matrix, such as, but not limited to, in a CMC component, the dark field contrast image provides structural ply information that is not available in the absorption image or the phase contrast image. For example, in one embodiment, the dark field contrast image displays individual 90 degree plies within the CMC component. In another embodiment, when the CMC component includes plies in various orientations, the component 103 is rotated orthogonally to the first grating 104 and/or the second grating 105 (e.g., orthogonally into the plane) to obtain information in a scattering direction. The orthogonal rotation of the component 103 provides information on plies other than the 90 degree plies, such as, but not limited to, 0 degree plies.

Displaying the individual plies provides information regarding conditions such as, but not limited to, ply buckling, inter-ply spacing, abnormal ply overlaps, directionality of the plies, other ply anomalies, or a combination thereof. For example, in one embodiment, the dark field contrast image displays ply buckling which is not displayed in either the absorption image or the phase contrast image. In another embodiment, the dark field contrast image displays both the plies and the free Si within the CMC component. The information from the 90 degree plies and the plies other than the 90 degree plies provide a complete picture of a ply make-up of the component 103 without cutting or otherwise damaging the component 103.

Together, the absorption image, the phase contrast image, and the dark field contrast image, which are all generated from a single scan with the system 100, display planes, volumetric information, plies, and foreign masses of disparate density. In one embodiment, the absorption image, the phase contrast image, and/or the dark field contrast image are overlaid with one or more color maps. The overlaid color maps provide a combined image for displaying the foreign masses within the component 103 from the phase contrast image and the plies from the dark field contrast image.

Displaying the density of foreign masses within the component 103, according to the method 200 described above, permits determining the amount and/or distribution of a specific element without destroying the component 103. The ability to determine the amount and/or distribution of a specific element without destroying the component 103 satisfies an unmet need in the art, specifically with regard to determining the amount and/or distribution of the free silicon within the SiC CMC component. Unlike previous methods, by not destroying the component 103, the method 200 satisfies another unmet need in the art, that of providing an ability to determine whether free Si is present, as well as the amount and/or distribution of any free Si within the component 103 prior to using the component 103 under operating conditions.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for elementally detecting variations in density within a component, the method comprising:
   providing a computed tomography device, comprising:
      a radiation source;
      a detector; and
      at least one grating between the radiation source and the detector;
   positioning the component between the radiation source and the detector;
   rotating the component orthogonally to the at least one grating;
   directing radiation from the radiation source to the detector to acquire information from the component;
   generating at least one phase contrast image and at least one dark field contrast image of the component corresponding to variations in density with the information from the component;
   incrementally rotating one or both of the component and the computed tomography device;
   correlating the variations in density to a foreign mass; and
   displaying foreign mass distribution within the component;
   wherein the rotating of the component orthogonally provides information relating to plies of the component other than 90 degree plies of the component and the incrementally rotating provides 360 degree views of the component.

2. The method of claim 1, wherein the component comprises a ceramic matrix composite.

3. The method of claim 1, further comprising determining an amount and a position of the foreign mass in the component from the phase contrast image and the dark field contrast image.

4. The method of claim 3, wherein the foreign mass is a free element.

5. The method of claim 4, wherein the free element is free silicon.

6. The method of claim 1, further comprising generating the dark field contrast images without damaging the component.

7. The method of claim 1, wherein the at least one grating comprises a first grating and a second grating, the first grating causing interference patterns.

8. The method of claim 7, wherein one of the at least one gratings is stepped to sample the interference patterns at the detector.

9. The method of claim 8, wherein the samples of the interference patterns are mapped as sinusoidal fringes.

10. The method of claim 1, further comprising forming a plurality of the phase contrast images and the dark field contrast images.

11. The method of claim 10, further comprising rotating the component with respect to the computed tomography device between generating each image in the plurality of phase contrast images and dark field contrast images.

12. The method of claim 10, further comprising rotating the computed tomography device with respect to the component between generating each image in the plurality of phase contrast images and dark field contrast images.

13. A method for detecting free elements in a ceramic matrix composite component, the method comprising:
   providing a computed tomography device, comprising:
      a radiation source;
      a detector;
      a first grating positioned between the radiation source and the detector; and
      a second grating positioned between the first grating and the detector;
   positioning the ceramic matrix composite component between the radiation source and the first grating;
   rotating the ceramic matrix composite component orthogonally to one or both of the first grating and the second grating;
   stepping the first grating or the second grating at each component position in the plurality of component positions to provide phase steps;
   incrementally rotating one or both of the ceramic matrix composite component and the computed tomography device to provide a plurality of component positions;
   directing radiation from the radiation source to the detector at each phase step of each component position in the plurality of component positions to acquire information from the ceramic matrix composite component;
   generating phase contrast and dark field contrast images corresponding to variations in density with the information from the ceramic matrix composite component;
   correlating the variations in density to at least one free element; and
   displaying distribution of the at least one free element within the ceramic matrix composite component
   wherein the rotating of the component orthogonally provides information relating to plies of the ceramic matrix composite component other than 90 degree plies of the ceramic matrix composite component and the incrementally rotating provides 360 degree views of the ceramic matrix composite component.

14. The method of claim 13, wherein the phase steps comprise 40 phase steps.

15. The method of claim 13, wherein the plurality of component positions comprises 360 positions.

* * * * *